United States Patent [19]

Sadowski

[11] 4,443,549

[45] Apr. 17, 1984

[54] PRODUCTION OF MONOCLONAL ANTIBODIES AGAINST BACTERIAL ADHESINS

[75] Inventor: Peter L. Sadowski, Eden Prairie, Minn.

[73] Assignee: Molecular Genetics, Inc., Minnetonka, Minn.

[21] Appl. No.: 428,622

[22] Filed: Oct. 7, 1982

Related U.S. Application Data

[63] Continuation-in-part of Ser. No. 312,993, Oct. 19, 1981.

[51] Int. Cl.³ ...................... A61K 39/40; C12N 15/00
[52] U.S. Cl. .......................................... 436/548; 424/9; 424/85; 424/87; 424/177; 435/70; 435/172; 435/240; 435/822; 435/849; 435/875; 260/112 R
[58] Field of Search .................. 436/548, 547, 548; 424/1.1, 85, 87, 177, 9; 435/68, 70, 172, 240, 241, 822, 849, 875; 260/112 R

[56] References Cited

U.S. PATENT DOCUMENTS 4,298,597 11/1981 Acres et al. .......................... 424/88
4,338,298 7/1982 Myers ................................... 424/92
4,343,792 8/1982 Gouet et al. .......................... 424/88

OTHER PUBLICATIONS

Soderstrom, T. et al., Scandinavian J. Immunology, vol. 15, (1), p. 121 (1982).
Cisar, J. O. et al., J. Reticuloendothelial Society, vol. 28, pp. 73-79 (12-1980) "Use of Monoclonal Antibodies ...".
Cisar et al., J. Immunology, vol. 127, No. 4, pp. 1318-1322, (10-1981) "Detection and Localization of a lectinon Actinomyces ...".
Norky et al., Archives of Virology, vol. 71, pp. 1-11 (1982).
Feldner, Jr. et al., Nature, vol. 298, pp. 765-767 (1982).
Isaacson et al.; Infection & Immunity 21(2): 392-397 (1978).
Parry and Porter, Immunology 34: 41-49 (1978).
Hu et al., Science 216: 313-314 (Apr. 1982).

Primary Examiner—Benjamin R. Padgett
Assistant Examiner—M. Moskowitz
Attorney, Agent, or Firm—Pennie & Edmonds

[57] ABSTRACT

Monoclonal antibodies specific for surface antigens of bacteria which act as adhesins between prokaryotic and eukaryotic cells and, in particular, K-99 pili, and methods for production thereof are described. These monoclonal antibodies may be used for the prophylactic and therapeutic treatment of diseases induced by adhesin-bearing pathogens in animals and humans, and for the diagnostic identification of adhesin-bearing bacteria.

43 Claims, No Drawings

PRODUCTION OF MONOCLONAL ANTIBODIES AGAINST BACTERIAL ADHESINS

CROSS-REFERENCE TO RELATED APPLICATIONS

This application is a continuation-in-part of application Ser. No. 312,993, filed Oct. 19, 1981 now pending.

TABLE OF CONTENTS

1. Introduction
2. Cross-reference to Related Applications
3. Background of the Invention
   3.1 Monoclonal Antibodies
   3.2 Bacterial Adhesins
   3.3 Adhesins of *Escherichia coli*
   3.4. Diarrheal Disease in Neonatal Farm Animals
   3.5 Diarrheal Disease in Humans
   3.6 Immunological Approaches to Prevention and Cure of Enterotoxigenic Diarrheal Disease
4. Summary of the Invention
5. Description of the Invention
   5.1 The Antigen
   5.2 Somatic Cells
   5.3 Myeloma Cells
   5.4 Fusion
   5.5 Isolation of Clones and Antibody Detection
   5.6 Cell Propagation and Antibody Production
   5.7 Uses for Adhesin-specific Monoclonal Antibodies
6. Examples
   6.1 Hyperimmunization Schedules
   6.2 Spleen Cell Preparation
   6.3 Myeloma Cell Preparation
   6.4 Fusion of Spleen and Myeloma Cells to Produce Hybrids
   6.5 Selection of Fused Cells
   6.6 Screening for Antibody-Producing Hybrids
   6.7 Limiting-Dilution Cloning
   6.8 Propagation of Hybrid Cells and Antibody Production
   6.9 Clinical Trials

INTRODUCTION

This invention relates to the production of antibodies specific for bacterial surface antigens (adhesins) involved in the adhesion of prokaryotic cells to eukaryotic cells. Many strains of pathogenic bacteria bear antigenic surface structures, such as pili, other proteins and glycoproteins as well as homopolymeric or heteropolymeric carbohydrate glycocalyces, by which the bacteria attach themselves to eukaryotic cell surfaces. The adhesin-mediated attachment permits bacterial proliferation in the invaded tissue which precedes the onset of disease. The diseases caused by adhesin-bearing pathogens are diverse and include diarrheal disease, respiratory diseases and burn infections. The present invention specifically relates to the production of monoclonal antibodies against bacterial adhesins. The monoclonal antibodies are capable of interfering with the adhesin-mediated attachment (and subsequent proliferation) of pathogens to eukaryotic cells and hence represent new therapeutic agents for the prevention and/or treatment of disease caused by bacteria bearing adhesins.

More particularly, this invention relates to the production of monoclonal antibodies against *Escherichia coli* adhesins, including pilus proteins and glycocalyx polysaccharides, by fused cell hybrids. Fimbrial surface proteins, such as K-99, K-88, 987P, F41, CFA/I and CFA/II and other pili, are adhesins involved in the attachment of certain enterobacteria, including enterotoxigenic strains of *E. coli*, to the mucosal lining of the small intestine of animals and humans. Fibrous capsular glycocalyx polysaccharides are another kind of enterobacterial surface adhesin that can function as a "cement" between prokaryotic cells and eukaryotic cells. Adhesin-mediated attachment and subsequent colonization are prerequisites for enterobacterial enterotoxin-induced diarrhea, a disease of great medical, especially veterinary, significance as it is frequently fatal to neonatal calves, lambs and piglets. The use of adhesion-specific monoclonal antibodies as prophylactic and therapeutic agents is a novel approach to prevention and treatment of enterotoxigenic diarrheal disease in animals and humans.

The monoclonal antibodies of this invention may be used in human or veterinary medicine or research for diagnostic, analytical and/or purification purposes. The invention provides a method for repeatedly producing large quantities of identical antibodies against adhesins that can serve as highly sensitive and specific probes in medical and veterinary diagnosis or microbiological research. Moreover, the invention provides a method for producing monoclonal antibodies against adhesins of bacteria that cause disease in humans or animals. The potential clinical and commercial importance of these antibodies, particularly in the veterinary community when applied to livestock immunoprophylaxis and immunotherapy, is tremendous.

BACKGROUND OF THE INVENTION

3.1 Monoclonal Antibodies

The technique for producing monoclonal antibodies was pioneered in the mid-1970's when Köhler and Milstein successfully fused spleen lymphocytes with malignant cells (myelomas) of bone marrow primary tumors [C. Milstein, Sci. Am. 243(4): 66–74 (1980)]. The method created a hybrid cell line, arising from a single fused cell hybrid, or clone, which possessed characteristics of both the lymphocytes and myeloma cell lines. Like the lymphocytes (taken from animals primed with sheep red blood cells as antigens), the fused hybrids, called hybridomas, secreted a single type of immunoglobulin specific to the antigen; moreover, like the myeloma cell lines, the hybrid cell lines were immortal. The combination of these two features has had a major impact in fields of research and medicine in which conventional antisera are used. Whereas antisera derived from vaccinated animals are variable mixtures of antibodies which never can be reproduced identically, monoclonal antibodies are highly specific immunoglobulins of a single type. The single type of immunoglobulin secreted by a hybridoma is specific to one and only one antigenic determinant on the antigen, a complex molecule having a multiplicity of antigenic determinants. For instance, if the antigen is a protein, an antigenic determinant may be one of the many peptide sequences [generally 6–7 amino acids in length (M. Z. Atassi, Molec. Cell. Biochem. 32: 21–43 (1980)] within the entire protein molecule. Hence, monoclonal antibodies raised against a single antigen may be distinct from each other depending on the determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

Monoclonal methods are generally applicable and have been used to produce antibodies to antigens other than the sheep red blood cells of Köhler and Milstein. For instance, it has been reported that monoclonal antibodies have been raised against tumor cells [U.S. Pat. No. 4,172,124], viruses [U.S. Pat. No. 4,196,265], and Group B Streptococci [R. Polin, Monoclonal antibodies against streptococcal antigen, pp. 353–359, in: R. Kennet, T. McKearn and K. Bechtol (editors), Monoclonal antibodies, hybridomas: a new dimension in biological analysis, Plenum Press, New York (1980)]. These antibodies are specific to each individual antigen against which they were raised and have no specificity for enterobacterial adhesins or enterobacterial strains bearing adhesins. Applicant believes that prior to this invention, no monoclonal antibodies have been produced that are specific to enterobacterial adhesin antigens involved in the colonization of enterotoxigenic bacteria in humans and animals. Furthermore, it is believed that no monoclonal antibodies have ever been utilized in the therapeutic or prophylactic treatment of diarrheal disease in humans or animals.

3.2 Bacterial Adhesins

The role of bacterial surface structures in pathogenesis has been extensively reviewed by Costerton et al. [CRC Crit. Rev. Microbiol., Sept., 1981: 303–338 (1981)]. Many of the surface structures described function as adhesins to facilitate the attachment and colonization of the pathogen in the invaded tissue. The adhesins discussed by Costerton et al. can serve as antigens against which the monoclonal antibodies of this invention can be raised to provide useful therapeutic agents for the prevention and treatment of diseases caused by adhesin-bearing pathogens. Thus, the Costerton et al. article, supra, is hereby incorporated by reference into the present specification.

3.3 Adhesins of Escherichia Coli

The surface of many gram-negative bacilli, e.g., *Escherichia coli*, is covered with filamentous structures, called pili or fimbriae. Pili are composed primarily of protein (pilin) with some associated carbohydrate and lipid; they act as antigenic determinants when injected into experimental animals. Certain pili, including K-99, K-88, 987P, and F41, mediate the colonization of *E. coli* in the small intestine of animals. Similarly, CFA/I and CFA/II pili mediate the colonization of *E. coli* in the small intestine of humans. Some bacterial cells lacking these pili, either through mutation or loss of the plasmid carrying the pilus gene, are incapable of colonizing the intestinal mucosa. Apparently, the pili on the outer surface of the bacterium adhere to the gut lining either through non-specific interactions with mucopolysaccharides or through specific interactions with intestinal epithelial cell receptors.

Some nonpiliated strains of *E. coli* are still capable of adhering to the gut lining of animals. This is due to the presence of another adherent structure on the cell surface. Specifically, some strains of *E. coli* are surrounded by a glycocalyx composed of a matrix of polysaccharide fibers that may be highly organized and intimately cell-associated to form a coherent capsule, or may be loosely cell-associated to form a partly detachable extracellular polysaccharide. The glycocalyx imparts adherent properties to the cell surface such that the bacteria are capable of colonizing the gut lining [J. W. Costerton, et al., CRC Crit. Rev. Microbiol. Sept., 1981: 303].

Adhesin-mediated anchorage is a prerequisite for the induction of diarrheal disease by certain strains of *E. coli* that secrete enterotoxins [S. Acres et al., Infec. Immun. 25: 121–126 (1979)]. Though the enterotoxin itself is the causative agent for the onset of diarrhea, it is believed that it cannot be produced in the gut in amounts sufficient to induce the disease if the bacteria have not colonized the intestinal lining first. Hence, any interference with bacterial adhesion and subsequent colonization will prevent the production of sufficient amounts of enterotoxin to induce diarrhea. The present applicant believes that monoclonal antibodies specific for the adhesin antigens of enterotoxigenic bacteria can interact with adhesins and interfere with cell anchorage. They, therefore, represent new and useful biological agents for the prevention and treatment of enterotoxin-induced diarrheal disease in humans and animals.

3.4 Diarrheal Disease in Neonatal Farm Animals

A significant number of new-born calves, lambs and piglets are infected with enterotoxigenic strains of *E. coli* and frequently die as a result of enterotoxin-induced diarrheal disease. The losses can be considerable if the neonates become infected within the first 48 to 72 hours after birth. During this period, the animals have no natural defenses against the infecting pathogen. Unless they are passively immunized by antibodies in their mother's milk, normally a rare event, they have limited resistance to survive the onset of the disease. Beyond three days postpartum, the neonates naturally acquire the capacity to withstand infections by enterotoxigenic *E. coli* and, like adult animals, are insensitive to the pathogen. They become insensitive because the peristaltic movement of the gut has developed sufficiently to flush the organisms from their intestines. It is therefore particularly critical that the calves, lambs and piglets be protected during the period of susceptibility to allow the intestinal peristalsis to develop. This protection can be accomplished by orally administering antibodies against the pathogen either immediately after birth to prevent infection or as soon after infection as possible to temporarily mitigate the disease or inhibit its onset while the neonatal intestinal tract develops. Monoclonal antibodies are ideally suited for this purpose since they can be raised in large quantities against specific antigens of the most common and potentially harmful enterotoxigenic bacteria and can be delivered orally to the animals to impart protection.

3.5 Diarrheal Disease in Humans

The adhesins of enterotoxigenic *E. coli* strains associated with diarrhea in humans were recently discovered and designated as CFA/I and CFA/II. The enterotoxigenic strains possessing these adhesins are considered a major cause of traveler's diarrhea and diarrhea among young children, particularly in developing countries [W. Gaastra and F. de Graaf, Microbiol. Rev. 46(2): 129–161 (1982)].

3.6 Immunological Approaches to Prevention and Treatment of Enterotoxigenic Diarrheal Disease Due to the high incidence, severe consequences, and potential deadliness of *E. coli* enterotoxin-induced diarrheal disease in new-born animals and in humans, a critical need for prophylactic and therapeutic agents exists. Traditional antibacterial approaches are usually ineffective since many of the enterotoxigenic strains of *E. coli* that infect calves, lambs, piglets and humans are highly resistant to antibiotics and other bactericidal compounds [I. Kornitzer et al., Ref. Vet. 36: 87-93 (1979)]. Immunological approaches, however, offer an interesting alternative to antibiotic regimens for the prevention and treatment of neonatal diarrheal disease. The bacterial pili are antigenic in nature; in addition, they play an important role in intestinal colonization and subsequent disease-induction. By interfering with the colonization, thereby preventing induction of diarrhea by the enterotoxin, antibodies against pili protect the host from infection. In those hosts that are infected by enterotoxigenic *E. coli,* the antibodies reduce the severity of the disease by preventing further proliferation of the microorganisms in the intestine.

Suckling neonates can be passively immunized by the transfer of maternal antibodies in the colostrum. Normally, however, adult cows, ewes and sows have very low or negligible pilus-specific antibody titers, even though they are insensitive to *E. coli* bearing K-99 or other fimbrial proteins. Several investigators [S. Acres et al., Infec. Immun. 25: 121-126 (1979); B. Nagy, Infec. Immun. 27: 21-24 (1980)] have approached this problem by subcutaneously vaccinating pregnant farm animals, specifically cows, with preparations of purified or partially purified K-99 pili. After the administration of several prepartum booster shots, the maternal antibody titers were sufficiently high at parturition to protect most suckling neonates challenged with K-99 positive enterotoxigenic *E. coli* shortly after birth. Though technically successful, this method suffers several practical drawbacks, including the tremendous expense and inconvenience of multiple maternal vaccinations, inability to guage the stage of gestation at which time vaccination should occur, variability of maternal antibody titers, limitation to prophylactic use only, and poor acceptance by the veterinary community.

To avoid some of these problems, Trainin et al. ["Oral Immunization of Young Calves Against Enteropathogenic *E. coli* with Immunocol", presented at the 11th International Cattle Disease Symposium, October, 1980] have formulated a product containing K-99 specific antibodies that can be orally administered to neonatal calves to prevent the onset of enterotoxin-induced diarrheal disease. While the product eliminates the need to vaccinate pregnant livestock and expands the use of antibodies to therapeutic as well as prophylactic treatments, it nonetheless possesses several shortcomings. Because it is prepared from the sera of cows vaccinated with whole bacterial cells of K-99 positive *E. coli* strains, the product contains antibodies with other specificities that may dilute the titer of anti-K-99 immunoglobulins and hence the potency of the preparation. Furthermore, a cow is required for antibody production, and, with each animal, immunoglobulin preparations vary qualitatively as to antibody spectrum and quantitatively as to anti-K-99 titers.

Adaptation of monoclonal techniques to the production of orally administrable, highly specific antibodies against pilus proteins represents a clear improvement over previous immunological approaches to the prevention and cure of enterotoxin-induced diarrheal disease. The fused cell hybrids made with these methods produce a single kind of antibody specific for the disease-mediating antigen. High titers of identical immunoglobulins are available in essentially limitless supply since the antibody-producing hybridomas can be cultured indefinitely in vitro or propagated in mice or other laboratory animals. The passive immunization strategies require costly maternal vaccinations or result in preparations (from adult animals) of non-specific antisera which may have to be purified extensively prior to use. The monoclonal approach, however, permits the quantitatively large-scale production of highly specific antibodies (requiring minimal purification, if any, when intended for animal use) in laboratory animals or culture vessels, relatively inexpensive and small-scale production units.

SUMMARY OF THE INVENTION

Prior to the present invention, there has been no report of a monoclonal antibody specific to an adhesin, either to a pilus protein or to any other surface antigen responsible for bacterial adhesion to and colonization of the mucocutaneous tissue of livestock or humans. Because adhesin-mediated colonization is required for the onset of pathogenesis, the monoclonal antibodies of this invention, by interfering with adhesion of pathogenic bacteria bearing adhesins to infected tissue, represent a new means of preventing or treating diseases and infections, including but not limited to diarrheal disease, respiratory tract disease, and burn infections, of humans and animals. The monoclonal antibodies may be delivered orally, intranansally, topically, or by some other route depending on the site of infection by the pathogen.

In a preferred embodiment, the present invention provides a method for producing monoclonal antibodies against pilus proteins and other adhesins of enterobacteria that cause diarrheal disease. The monoclonal antibodies can be administered orally for prophylactic or therapeutic purposes to adult and infant humans and/or neonatal calves, lambs and piglets during the postpartum period of disease susceptibility. To achieve prophylaxis in animals, the anti-adhesin monoclonal antibody can be mixed with colostrum, or any pharmaceutical carrier suitable for oral administration and compatible with the monoclonal antibody and the gastrointestinal tract of the animal, and fed to uninfected neonates until they develop their own natural resistance to enterotoxigenic bacteria. Administration of the antibody by traditional intramuscular and intravenous routes is generally inefficacious. With the monoclonal antibodies of this invention, prophylactic treatment in animals can begin and is effective the moment an outbreak of enterotoxigenic bacteria is suspected among neonates. The immediate effectiveness of the administration of the monoclonal antibodies is a notable improvement over the more traditional immunological alternative of immunizing nursing mothers at the time of outbreak. Because there is a lag period for raising the maternal antibody titers sufficiently high to protect sucklings, immunization of nursing mothers is ineffective. In addition, the oral administration of monoclonal antibodies eliminates the need to immunize all nursing mothers when an outbreak occurs. A further advantage of the anti-adhesin monoclonal antibodies is their potential as therapeutic agents. While most immunological approaches to controlling enterotoxin-induced diarrheal disease in farm animals have been prophylactic (for instance, the immunization of pregnant livestock so that specific antibodies will be transmitted by the colostrum from mother to neonates) the present invention provides an immunological agent which, because it can be delivered directly to the infected animal, can be used as an immunotherapeutic agent as well. Therapeutic use can ensue upon the onset of infection and can continue until the sucklings recover and pass the stage of susceptibility.

In humans, therapeutic treatment can be begun upon observation of the symptoms of diarrheal disease. Prophylactic treatment may be undertaken when a child or adult is suspected of exposure to organisms known to cause diarrheal illnesses. For human treatment, any suitable pharmaceutical carrier compatible with the monoclonal antibody and the human gastrointestinal tract may be used.

The present invention also provides a method of producing monoclonal antibodies of general importance in human and veterinary medicine and microbiological research. The anti-adhesin monoclonal antibody can be used as a diagnostic probe to identify pathogenic, for instance enterotoxigenic, bacteria among the bacterial population normally present. The ultraspecific identification provided by the antibody-antigen interaction affords rapid diagnosis and therefore facilitates prompt administration of prophylactic or therapeutic treatments. The monoclonal antibody-antigen interaction also may be used to detect antigenic drift where a conventional antisera would not. The high specificity of the immunological interaction also makes the anti-adhesin monoclonal antibody an important laboratory tool for the quantitative and qualitative analysis or purification of the adhesin in microbiological, bacteriological or biochemical research. Thus, a biological sample containing the adhesin can be contacted with anti-adhesin antibodies to form adhesin-antibody complexes which can be separated from the sample. The adhesin-antibody complexes can be further dissociated to recover purified adhesin.

Because the anti-adhesin monoclonal antibody is produced by hybridoma techniques, the present invention provides an immortal cell line capable of consistently producing high titers of a single specific antibody against the bacterial adhesin. This is a distinct advantage over the traditional technique of raising antibodies in immunized animals where the resulting sera contain multiple antibodies of different specificities that vary in both type and titer with each animal, and, in individual animals, with each immunization.

The invention contemplates the extension of the hybridoma technique to the production of monoclonal antibodies to other bacterial adhesins or surface antigens similarly responsible for colonization in other host species. The present invention further comtemplates pharmaceutical preparations containing several monoclonal antibodies each directed to the adhesin antigens of different bacterial strains.

DESCRIPTION OF THE INVENTION

5.1 The Antigen

The outer surfaces of pathogenic bacterial cells are involved in the causation of some diseases. Studies of this involvement have implicated certain antigenic adhesins, including pili and other proteins, glycoproteins and glycocalyx polysaccharides, in the adhesion and colonization of bacteria which proliferate in mucocutaneous tissues of animals and humans.

There are several antigenic pilus proteins that mediate the attachment of enterotoxigenic bacteria, and in particular, enterotoxigenic *Escherichia coli* (ETEC), to the intestinal mucosa of mammals. These include the K-99 antigen on bovine, ovine and some porcine ETEC, the F41 antigen on bovine ETEC, the K-88 and 987P antigens on porcine ETEC and the so-called colonization factor antigens (CFA/I and CFA/II) on human ETEC. Depending on the antibody desired, any one of these serologically distinct pilus proteins or other adhesins is a suitable antigen with which to prime animals, such as mice, to obtain antibody-producing somatic cells for fusion. In other words, animals can be immunized against the antigen by administering an injection or series of injections (an initial shot and one or more boosters) of the adhesin over the course of several weeks before taking the antibody-producing somatic cells from the animals. The antigen may be administered in an impure form such as the original bacteria(um) bearing the adhesin or a part thereof bearing the adhesin or as the purified adhesin or an immunogenic fragment thereof. In the example of the present case, a preparation of K-99 antigen purified from *E. coli* strain 1474 by standard techniques [R. Isaacson, Infec. Immun. 15: 272-279 (1977)] was used. Other strains of enterotoxigenic *E. coli*, including *E. coli* strains B41, B42 and B44, bear pili that can also serve as sources of antigen to be used to raise monoclonal antibodies.

Other pili besides those of *E. coli* are immunogenic and function as adhesins, for instance the pili of *Pseudomonas aeruginosa*. Further, other proteins besides pili are involved in adhesion of prokaryotic to eukaryotic cells. For instance, the M protein of Group A Streptococci is an adhesin that can serve as antigen. Also, the bacterial glycocalyx has been shown to be a virulence factor in pathogens as diverse as Actinomyces, Bacteroides, Hemophilus, Pseudomonas, Salmonella, Streptococcus, Staphylococcus and numerous others (see Costerton et al., supra). The diseases caused by some of these pathogens result from colonization of the mucosa aided in part by the glycocalyx produced by the bacteria. Glycocalyx carbohydrates are suitable for use as antigens.

5.2 Somatic Cells

Somatic cells with the potential for producing antibody and in particular B cells are suitable for fusion with a B-cell myeloma line. Those antibody-producing cells undergoing mitosis fuse preferentially. Lymph nodes and spleens of primed animals are convenient sources; it is best to use whichever lymphatic organ gives optimal activity in the particular fusion system, though little is known about the factors influencing fusion optimization. Once-primed or hyperimmunized animals can be used as a source of antibody-producing lymphocytes. Mouse and rat lymphocytes give a higher percentage of stable fusions with the mouse myeloma lines described below. However, the use of rabbit, human and frog cells is also possible. In the preferred embodiment, hyperimmunized mouse spleen cells are used to make the fused cell hybrids.

5.3 Myeloma Cells

Specialized myeloma cell lines have been developed from lymphoctye tumors for use in hybridoma-producing fusion procedures [G. Köhler and C. Milstein, Eur. J. Immunol. 6: 511-519 (1976); M. Shulman et al., Nature 276: 269-270 (1978)]. The cell lines have been developed for at least three reasons. The first is to facilitate the selection of fused hybridomas among unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of cell lines is for their suitability and efficiency for fusion.

Several myeloma cell lines may be used for the production of fused cell hybrids, including P3/X63-Ag 8, P3/NSI/1-Ag 4-1, Sp2/0-Ag14 and S194/5.XXO.BU.1. The P3/X63-Ag 8 and P3/NSI/1-Ag 4-1 cells lines have been described by Köhler and Milstein [Eur. J. Immunol. 6: 511–519 (1976)]. Shulman et al. [Nature 276: 269–270 (1978)] developed the Sp2/O-Ag14 myeloma line. The S194/5.XXO.BU.1 myeloma line was reported in an article by Trowbridge [J. Exp. Med. 148: 313 (1979)]. In the example of the present invention, P3/NSI/1-Ag 4-1, a non-secreting mutant of P3/X63-Ag 8 (derived from BALB/c mice) is the preferred cell line.

5.4 Fusion

Methods for generating hybrids of antibody-producing spleen or lymph node cells and myeloma cells usually comprise mixing somatic cells with myeloma cells in a 10:1 proportion (though the proportion may vary from 20:1 to 1:1), respectively, in the presence of an agent or agents that promote the fusion of cell membranes. It is preferred that the same species of animal serve as the source of the somatic and myeloma cells used in the fusion procedure. Fusion methods have been described by Köhler and Milstein [Nature 256: 495–497 (1975) and Eur. J. Immunol. 6: 511–519 (1976)], and by Gefter et al. [Somatic Cell Genet. 3: 231–236 (1977)]. The fusion-promoting agents used by those investigators were Sendai virus and polyethylene glycol (PEG), respectively. The fusion procedure of the example of the present invention is a modification of the method of Gefter et al. [supra]; dimethyl sulfoxide (DMSO), another agent affecting cell membranes, in addition to PEG, is added to the mixture of mouse spleen and myeloma cells to promote the formation of fused cell hybrids, or hybridomas.

5.5 Isolation of Clones and Antibody Detection

Because fusion procedures produce viable hybrids at very low frequency (e.g., when spleens are used as a source of somatic cells, only one hybrid is obtained for roughly every $2 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybridomas but prevent the growth of the myeloma cells which normally would go on dividing indefinitely. (The somatic cells used in the fusion do not maintain viability in in vitro culture and hence do not pose a problem.) In the example of the present invention, myeloma cells lacking hypoxanthine phosphoribosyl transferase (HPRT−) were used. These cells are selected against in hypoxanthine/aminopterin/-thymidine (HAT) medium, a medium in which the fused cell hybrids survive due to the HPRT-positive genotype of the spleen cells. The use of myeloma cells with different genetic deficiencies (e.g., other enzyme deficiencies, drug sensitivities, etc.) that can ben selected against in media supporting the growth of genotypically competent hybrids is also possible.

Several weeks are required to selectively culture the fused cell hybrids. Early in this time period, it is necessary to identify those hybrids which produce the desired antibody so that they may be subsequently cloned and propagated. Generally, around 10% of the hybrids obtained produce the desired antibody, although a range of from 1 to 30% is not uncommon. The detection of antibody-producing hybrids can be achieved by any one of several standard assay methods, including enzyme-linked immunoassay and radioimmunoassay techniques which have been described in the literature [R. Kennet, T. McKearn and K. Bechtol (editors), Monoclonal antibodies, hybridomas: a new dimension in biological analyses, pp. 376–384, Plenum Press, New York (1980)]. The detection method used in the example of the present invention was an enzyme-linked immunoassay employing a peroxidase-conjugated anti-mouse immunoglobulin.

5.6 Cell Propagation and Antibody Production

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. Th body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

5.7 Uses for Adhesin-Specific Monoclonal Antibodies

Monoclonal antibodies specific to colonization-mediating adhesins can be used clinically for the prevention or treatment of diseases caused by pathogenic bacteria bearing adhesins. For example, monoclonal antibodies specific for surface pili of enterotoxigenic bacteria such as *E. coli* can be used clinically for the prevention and/or treatment of enterotoxin-induced diarrheal disease in neonatal animals, including calves, lambs and piglets, and in human adults and children. The mode of administration of these monoclonal antibodies is preferably oral. The monoclonal antibodies may be suspended or dissolved in any of several suitable liquid vehicles and delivered to the neonate by one of several oral means. The ascites fluid of the animal or the in vitro culture medium in which the antibody-producing clones were propagated are pharmaceutically acceptable liquid carriers for animals and may be used directly without purification or concentration though a clarification step may be desirable. In some instances, and particularly where human treatment is involved, purification may be desired or required pursuant to governmental regulation. Provided the monoclonal antibody is present in a pharmacologically effective dosage, other liquid compositions are also pharmaceutically suitable, including mixtures of antibodies and colostrum, antibodies and skimmed milk and/or antibodies and solutions of bovine serum albumin (in which the albumin concentration is from 1 to 20 mg/ml).

In animals, these anti-pilus liquid monoclonal antibody compositions may be administered orally to the new-borns by such modes as intubation, bottle feeding or capsular form. As a preventative measure, administration of the antibody composition may begin immediately or a few hours after birth and continue until the animal has acquired its own defenses to infecting pathogens. Alternatively, the antibody may be administered only when an outbreak of enterotoxigenic bacteria has occurred among a group of farm animals to treat the infected livestock and prevent the spread of the disease to other animals.

In humans, the monoclonal antibody compositions are preferably administered in capsular form, though any compatible carrier may be used.

The adhesin-specific monoclonal antibodies are also useful for medical and research purposes. For instance, these monoclonal antibodies can be used diagnostically to detect with great accuracy the presence of adhesin-bearing strains among a general population of bacteria. Other applications include the use of adhesin-specific monoclonal antibodies in affinity chromatography systems for the super-selective purification of adhesin or in assay systems for the quantitative measurement of adhesins.

EXAMPLES

6.1 Hyperimmunization Schedules

To obtain spleen cells which produce antibodies to purified K-99 pilus protein, BALB/c mice were hyperimmunized with the antigen (derived from enterotoxigenic *E. coli* strain 1474 of calf origin) according to two different schedules, though other immunization schedules may be used with similar success. By one schedule, the mice received dorsal, subcutaneous 0.5 ml injections of antigen (50 ug, where ug=microgram) and Freund's Complete Adjuvant (1:1). Approximately twelve weeks after the initial priming, the mice were boosted twice with intraperitoneal and intravenous injections of antigen, respectively; two weeks intervened between the booster injections which contained antigen (50 ug, preferably 10 to 50 ug) in 0.5 ml of TSE buffer (Tris-Salt-EDTA, containing 10 mM Tris, 150 mM sodium chloride and 1 mM ethylenediaminetetraacetic acid, respectively). Three days after the second boosting, the mice were sacrificed and their spleens were used as described in Section 6.2.

In another experiment, BALB/c mice were primed as in the example above. Twelve weeks later, the animals received an intraperitoneal booster injection of antigen (5 ug) in 0.5 ml of TSE buffer. This was repeated approximately two weeks later. Spleens were taken from the sacrificed mice three days after the boosting and were processed further by the method described below.

6.2 Spleen Cell Preparation

Spleens of hyperimmunized BALB/c mice were removed under sterile conditions and washed in DMEM (Dulbecco's minimal essential medium) serum-free medium (Gibco, Grand Island, N.Y.). Spleens were macerated on a metal screen after which procedure the cells were resuspended in DMEM medium (10 ml/spleen) and centrifuged. The supernatant fraction was removed and the spleen cells were resuspended in DMEM serum-free medium. The cell number was determined directly by microscopic count before mixing with myeloma cells (See Section 6.4).

6.3 Myeloma Cell Preparation

BALB/c mouse lymphocyte tumor cells of the P3/NSI/1-Ag 4-1 cell line (a mutant, 8-azaguanine-resistant, non-secreting line derived from P3/X63-Ag 8) were maintained in a 5–10% carbon dioxide atmosphere in DMEM medium containing 5–15% FCS (fetal calf serum) and 15 ug/ml 8-azaguanine, supplemented with 100 U/ml penicillin and 100 ug/ml streptomycin. The myeloma cells were maintained in log phase (cell density never to exceed about $2 \times 10^5$ cells/ml). Before the cell fusion procedure (Section 6.4), the myeloma cells were washed by centrifugation in DMEM serum-free medium, resuspended in the same medium, and counted microscopically.

6.4 Fusion of Spleen and Myeloma Cells to Produce Hybrids

After the spleen and myeloma cells were washed in DMEM serum-free medium and counted, they were mixed in round bottom plastic tubes; the ratio of spleen to myeloma cells in the mixture was 10:.1 The cell suspensions were centrifuged at $250 \times g$ for 5 minutes at room temperature. After carefully aspirating all of the supernatant fraction, the cell pellets were gently resuspended for 1 to 2 minutes in 0.2 to 2.0 ml of a solution containing 35–40% (v/v) PEG, 15% (v/v) DMSO and 45–50% (v/v) DMEM serum-free medium. To the cell suspension, 18 to 20 ml of DMEM serum-free medium was added slowly dropwise with constant agitation of the tube. (This procedure took from 4 to 8 minutes.) The suspensions were centrifuged as above. The cell pellets were resuspended in 50 ml of DMEM containing either 20% horse serum or 15% fetal calf serum. Additional supplements were penicillin, streptomycin, and HAT ingredients (12 mM hypoxanthine, 9 uM aminopterin and 8 mM thymidine). The fused cells were then plated out into the wells of TC 24 macrotiter plates (Costar Cambridge, Mass.). This medium is selective for fused cells. Hence, hybrids will grow while unfused spleen and myeloma cells die out of the culture.

6.5 Selection of Fused Cells

The fusion procedure described in Section 6.4 was followed by a 2 to 4 week culturing period that allowed for the outgrowth of hybrid cells. As needed, about half of the HAT medium in the wells of the macrotiter plates was removed and replaced with fresh HAT medium. After about 2–3 weeks, the type of medium fed to the cells was changed from HAT medium to medium without HAT. Screening was initiated at two weeks post-fusion as described in Section 6.6.

6.6 Screening for Antibody-Producing Hybrids

An enzyme-linked immunoassay was used to screen fused cells for antibody production. The wells of microtiter plates (96 well, Falcon) were coated with 0.1 ml of K-99 pilus protein antigen (5 ug/ml in 60 mM sodium carbonate, pH 9.6) for 15 to 30 minutes at 37° C. The liquid was removed and the plates were washed three times with a Tween 20 (polyoxethylene sorbitan monolaurate) buffer [H. Friedman (editor), Manual clinical immunology, pp. 506–512 (1976)]. After washing, 0.1 ml of culture fluid was taken from the wells of the macrotiter plates in which the fused cells had been selected and delivered to the wells of the microtiter plates. The plates were incubated for 30 minutes at room temperature and subsequently washed three times with the Tween buffer. The next step of the procedure was the addition of 0.1 ml of peroxidase-conjugated anti-mouse IgG (heavy and light chain specific) immunoglobulin (Cappel Laboratories, Cochranville, Pa.) diluted 1:1000 in Tween buffer to the microtiter wells. The plates were swirled on a reciprocating shaker for 30 minutes at room temperature, and were washed 3 times with Tween buffer thereafter. With the enzyme so bound to any anti-K-99 antibody, 0.1 ml of the substrate solution [OPD buffer, pH 5.0: 25 mM citrate and 50 mM dibasic sodium phosphate containing hydrogen peroxide (40 ul 30% $H_2O_2$/100 ml buffer) and orthophenyl diamine (40 mg/100 ml buffer)] was added to the wells and the plates were swirled for 15 minutes at room temperature. Upon addition of 2.5 M sulfuric acid to stop the colorimetric enzyme reaction 15 minutes later, the plates were photographed and the positive wells were noted. The cells formed in one such positive well were named 2BD4E4. The corresponding fused cells in the original selective macrotiter plates were then cloned.

6.7 Limiting-Dilution Cloning

Approximately 12 hours before cloning, feeder cells from spleens of non-immunized mice were macerated and the cells were suspended in either 20% horse serum or 15% fetal calf serum to a final cell concentration of $3 \times 10^6$ cells/ml. Into the wells of microtiter plates, 0.1 ml of the spleen cells was delivered. This seeding procedure provided an environment suitable for the growth of fused cell hybrids.

Cloning was performed by counting the fused cells in the wells of the macrotiter plates used for selection of hybrids as described in Section 6.5, diluting them in supplemented DMEM medium to a concentration whereby every second well of the microtiter plate would receive one cell, and adding 0.1 ml of the diluted fused cells to the microtiter wells containing the seeded spleen cells. After 2–4 weeks of culturing (during which time the medium was replenished periodically and the seeded spleen cells lost viability) hybrid clones appeared in the microtiter wells before propagation. (See Section 6.8.) The clones were rescreened for antibody production using the enzyme-linked immunoassay system.

6.8 Propagation of Hybrid Cells and Antibody Production

After the clones had grown to confluence in the microtiter plates, they were transferred to macrotiter plates and cultured to a cell density suitable for injection into mice (about $10^6$ cells per injection). Syngeneic mice were injected with doses of individual clones. After development of noticeable ascites, the mice were tapped. The ascites fluid generally contained anti-K-99 monoclonal antibodies in concentrations such that the fluid could be diluted $10^5$–$10^6$-fold and still produce a positive reaction in the enzyme-linked immunoassay system.

6.9 Clinical Trials

Ten piglets were obtained by caesarean section from a single, common sow on or about the 115th day of gestation. The new-borns were colostrum deprived (hence, no maternal antibody passed to the new-borns), and kept in a pathogen-free environment for 2–3 hours. The piglets were then intubated and given a specified volume of tryptic soy broth containing K-99 positive E. coli followed by a specific volume of monoclonal antibody (from ascites fluid clarified by centrifugation) in a diluant, the composition of which appears in Table 1. The tube was cleared with a small burst of air following administration of E. coli and antibody. The piglets were kept in individual cages, in the same room, and fed SPF-Lac Sow Milk Replacer [Borden (Columbus, Ohio); SPF stands for "specific pathogen-free"]. At no time were piglets given maternal milk. The study ran for 6 days during which time the individual caring for the piglets had no idea which animals served as controls or experimental animals.

TABLE 1

Results of K-99 Clinical Trial of Monoclonal Antibody Against K-99

| GROUP | CONTROLS | | | TEST |
|---|---|---|---|---|
| | One | Two | Three | Four |
| No. Piglets | 2 | 2 | 2 | 4 |
| Tryptic Soy Broth | + | + | + | + |
| K-99 positive E. coli | − | + | + | + |
| Diluant (20 mMTris with 20 mg/ml Bovine serum albumin, pH 7.2) | + | + | + | + |
| Unrelated monoclonal antibody | − | − | + | − |
| K-99 monoclonal antibody | + | − | − | + |
| Survivors after 6 days | 1* | 0 | 0 | 3** |

*The death of one piglet in Group One was not due to K-99 positive E. coli diarrheal disease.
**One piglet out of four died of K-99 positive E. coli diarrheal disease.

The K-99 positive E. coli strain B41 used in the clinical test had been grown on Minca plates by standard procedures [P.A.M. Guinee et al., Infec. Immun. 15(2): 676–678, (1977)]. Plate cultures were scraped, resuspended in medium containing glycerol, and frozen in aliquots. A slide agglutination test was used to check E. coli for presence of K-99 antigen. Approximately $1.3 \times 10^{10}$ E. coli (determined by plate count) were given to each animal. The piglets therefore received a single dose of antigen (K-99 positive E. coli) and a single dose of antibody (monoclonal K99) in that sequence, respectively.

The results of the clinical trial are presented in Table 1. The efficacy of the monoclonal antibody in preventing the onset of diarrheal disease and subsequent death is clearly shown in the "TEST" column. Three out of the four piglets receiving a dose of anti-K-99 pilus protein monoclonal antibody, after the administration of K-99 positive E. coli, survived six days.

A cell line, 2BD4E4, as described herein has been deposited with the American Type Culture Collection, Rockville, Md., and has been assigned accession number ATCC No. HB8178. The invention described and claimed herein is not to be limited in scope by the cell line deposited, since the deposited embodiment is intended as a single illustration of one aspect of the invention and any equivalent cell lines which produce a functionally equivalent monoclonal antibody are within the scope of this invention. Indeed, various modifications of the invention in addition to those shown and described herein will become apparent to those skilled in the art from the foregoing description. Such modifications are also intended to fall within the scope of the appended claims.

I claim:

1. A process for producing monoclonal antibodies against an adhesion of a pathogenic bacterium, which adhesin mediates attachment of said bacterium to mucocutaneous tissue, comprising: propagating a hybridoma formed by fusing a cell capable of producing antibodies against an adhesin of a pathogenic bacterium, which adhesin mediates attachment of said bacterium to mucocutaneous tissue, with a myeloma cell and harvesting the antibodies produced by said hybridoma.

2. The process of claim 1 wherein said adhesin is a protein adhesin.

3. The process of claim 1 wherein said adhesin is a pilus.

4. The process of claim 1 wherein said adhesin is a glycocalyx polysaccharide.

5. The process of claim 1 wherein said hybridoma is propagated in vitro.

6. The process of claim 1 wherein said hybridoma is propagated in vivo.

7. The process of claim 1 wherein said cell capable of producing antibodies against an adhesin of a pathogenic bacterium is selected from the group consisting of spleen cells and lymph node cells.

8. The process of claim 7 wherein said spleen is mouse spleen and said myeloma is mouse myeloma.

9. The process of claim 1 wherein said cell capable of producing antibodies against an adhesin of a pathogenic bacterium is obtained from an animal immunized with a pilus adhesin, an immunogenic fragment thereof, or a bacterium, or part thereof, bearing a pilus adhesin.

10. The process of claim 1 wherein said cell capable of producing antibodies against an adhesin of a pathogenic bacterium is obtained from an animal immunized with a glycocalyx adhesin, an immunogenic fragment thereof, or a bacterium, or part thereof, bearing a glycocalyx adhesin.

11. The process of claim 1 wherein the bacterium is *Escherichia coli*.

12. The process of claim 1 wherein the bacterium is *Pseudomonas aeruginosa*.

13. The process of claim 3 wherein the pilus is selected from the group consisting of K-99, K-88, 987P, F41, CFA/I and CFA/II pili.

14. The process of claim 3 wherein the pilus is K-99 pilus.

15. A process for producing monoclonal antibodies against an adhesin of a pathogenic bacterium, which adhesin mediates attachment of said bacterium to mucocutaneous tissue, comprising: (a) propagating a hybridoma (i) formed by fusing a P3/NSI/1-Ag4-1 myeloma cell with a murine cell capable of producing antibodies against an adhesin of a pathogenic bacterium, which adhesin mediates attachment of said bacterium to mucocutaneous tissue, said murine cell having been obtained from a BALB/c mouse immunized with a bacterial adhesion and (ii) isolated after in vitro culturing in selective HAT medium; and (b) harvesting the antibodies produced by said hybridoma.

16. The process of claim 15 wherein said hybridoma is propagated in vitro.

17. The process of claim 15 wherein said hybridoma is propagated in vivo.

18. The process of claim 15 wherein said adhesin is the K-99 pilus.

19. A continuous cell line which produces monoclonal antibodies against an adhesin of a pathogenic bacterium, which adhesin mediates attachment of said bacterium to mucocutaneous tissue, comprising a hybridoma formed by fusing a cell capable of producing antibodies against an adhesin of a pathogenic bacterium, which adhesin mediates attachment of said bacterium to mucocutaneous tissue, with a myeloma cell.

20. The cell line of claim 19 wherein said adhesin is a pilus.

21. The cell line of claim 19 wherein said adhesin is K-99 pilus.

22. Hybridoma cell line 2BD4E4, ATCC Number HB8178, formed by fusing a P3/NSI/1-Ag 4-1 murine myeloma cell with a murine spleen cell obtained from a BALB/c mouse immunized with K-99 pili, which hybridoma cell line produces monoclonal antibodies against a K-99 pilus.

23. The cell line of claim 19 wherein said adhesin is a protein adhesin.

24. The cell line of claim 19 wherein said adhesin is a glycocalyx polysaccharide.

25. Monoclonal antibodies against an adhesin of a pathogenic bacterium, which adhesin mediates attachment of said bacterium to mucocutaneous tissue.

26. Monoclonal antibodies against K-99 pilus produced by the cell line of claim 22.

27. A pharmaceutical composition comprising monoclonal antibodies against an adhesin of a pathogenic bacterium, which adhesin mediates attachment of said bacterium to mucocutaneous tissue, and a pharmaceutical carrier therefor.

28. The pharmaceutical composition of claim 27, wherein the adhesin is a pilus.

29. The pharmaceutical composition of claim 27, wherein the adhesin is a protein adhesin.

30. The pharmaceutical composition of claim 27, wherein the adhesin is a glycocalyx polysaccharide.

31. The pharmaceutical composition of claim 27, wherein the pharmaceutical carrier is suitable for oral administration to animals.

32. The pharmaceutical composition of claim 28, wherein the pharmaceutical carrier is suitable for oral administration to animals.

33. The pharmaceutical composition of claim 31 or 32, wherein said carrier is maternal colostrum.

34. The pharmaceutical composition of claim 31 or 32, wherein said carrier is Tris buffer containing bovine serum albumin.

35. The pharmaceutical composition of claim 31 or 32, wherein said carrier is skimmed milk.

36. The pharmaceutical composition of claim 31 wherein said animals are selected from the group consisting of calves, lambs and piglets.

37. The pharmaceutical composition of claim 27, wherein the pharmaceutical carrier is suitable for topical administration to a host.

38. The pharmaceutical composition of claim 27, wherein the pharmaceutical carrier is suitable for administration to the respiratory tract of a host.

39. A process for producing monoclonal antibodies against an adhesin of a pathogenic bacterium, which adhesin mediates attachment of said bacterium to mucocutaneous tissue, comprising: propagating a hybridoma formed by fusing a cell capable of producing antibodies against an adhesin of a pathogenic bacterium, which adhesin mediates attachment of said bacterium to mucocutaneous tissue, the pathogenicity of said bacterium being dependent on noninvasive, adhesin-mediated attachment to and subsequent proliferation on the surface of mucocutaneous tissue, with a myeloma cell and harvesting the antibodies produced by said hybridoma.

40. The process of claim 39 wherein the mucocutaneous tissue is mammalian intestinal lining.

41. Monoclonal antibodies against an adhesin of a pathogenic bacterium, which adhesin mediates attachment of said bacterium to mucocutaneous tissue, the pathogenicity of said bacterium being dependent on noninvasive, adhesin-mediated attachment to and subsequent proliferation on the surface of mucocutaneous tissue.

42. The monoclonal antibodies of claim 41 wherein the mucocutaneous tissue is mammalian intestinal lining.

43. A continuous cell line which produces monoclonal antibodies against an adhesin of a pathogenic bacterium, which adhesin mediates attachment of said bacterium to mucocutaneous tissue, comprising a hybridoma formed by fusing a cell capable of producing antibodies against an adhesin of a pathogenic bacterium, which adhesin mediates the attachment of said bacterium to mucocutaneous tissue, the pathogenicity of said bacterium being dependent on noninvasive, adhesin-mediated attachment to and subsequent proliferation on the surface of mucocutaneous tissue, with a myeloma cell.

* * * * *